United States Patent
Young (10) Patent No.: US 9,368,325 B2
(45) Date of Patent: Jun. 14, 2016

(54) TEM SAMPLE PREPARATION

(71) Applicant: FEI Company, Hillsboro, OR (US)

(72) Inventor: Richard J. Young, Beaverton, OR (US)

(73) Assignee: FEI Company, Hillboro, OR (US)

( * ) Notice: Subject to any disclaimer, the term of this patent is extended or adjusted under 35 U.S.C. 154(b) by 0 days.

(21) Appl. No.: 14/692,509

(22) Filed: Apr. 21, 2015

(65) Prior Publication Data

US 2015/0325409 A1 Nov. 12, 2015

Related U.S. Application Data

(63) Continuation of application No. 13/930,911, filed on Jun. 28, 2013, now Pat. No. 9,040,908.

(51) Int. Cl.
| | | |
|---|---|---|
| *H01J 37/317* | (2006.01) | |
| *H01J 37/305* | (2006.01) | |
| *H01J 37/20* | (2006.01) | |
| *H01J 37/28* | (2006.01) | |

(Continued)

(52) U.S. Cl.
CPC ............... *H01J 37/317* (2013.01); *G01N 1/32* (2013.01); *H01J 37/20* (2013.01); *H01J 37/28* (2013.01); *H01J 37/3023* (2013.01); *H01J 37/3053* (2013.01); *H01J 37/3178* (2013.01); *H01J 2237/2802* (2013.01); *H01J 2237/31745* (2013.01); *H01J 2237/31749* (2013.01)

(58) Field of Classification Search
USPC .......................... 250/304, 306, 307, 309, 311
See application file for complete search history.

(56) References Cited

U.S. PATENT DOCUMENTS

| | | |
|---|---|---|
| 5,435,850 A | 7/1995 | Rasmussen |
| 5,851,413 A | 12/1998 | Casella et al. |
| 6,963,068 B2 | 11/2005 | Asselbergs et al. |

(Continued)

FOREIGN PATENT DOCUMENTS

WO 2007008238 A1 7/2007

OTHER PUBLICATIONS

Unknown, "AutoProbe 200 Nano-Manipulator System from Omniprobe," http://www.azonano.com/equipment-details.aspx?EquipID=391, obtained Nov. 13, 2013, 3 pages.
Unknown, "EasyLift NanoManipulator System," http://aged.fei.com/upgrades/item.aspx?itemid-34359740191, obtained Nov. 13, 2013, 1 page.

(Continued)

*Primary Examiner* — Kiet T Nguyen
(74) *Attorney, Agent, or Firm* — John B. Kelly; Scheinberg & Associates (57) ABSTRACT

A method and apparatus for altering the orientation of a charged particle beam sample is presented. Embodiments of the method includes providing a first work piece on a sample stage having a sample stage plane, the first work piece including a lamella plane in a first orientation. A sample is milled from the first work piece using an ion beam so that the sample is substantially free from the first work piece. A probe is attached to the sample, the probe including a shaft having a shaft axis, the shaft axis oriented at a shaft angle in relation to the sample stage plane, the shaft angle being non-normal to the sample stage plane. The probe is rotated about the shaft axis through a rotational angle so that the lamella plane is in a second orientation. The sample is attached to or placed on the sample on either the first work piece, the first work piece being the work piece from which the sample was milled, or on a second work piece, the second work piece being a work piece from which the sample was not milled. The sample is thinned using the ion beam to form a lamella, the lamella being oriented in the lamella plane.

13 Claims, 8 Drawing Sheets

(51) Int. Cl.
*G01N 1/32* (2006.01)
*H01J 37/302* (2006.01)

(56) References Cited

U.S. PATENT DOCUMENTS

| | | | |
|---|---|---|---|
| 7,615,745 | B2 | 11/2009 | Schampers et al. |
| 9,040,908 | B2 | 5/2015 | Young |
| 2008/0073535 | A1 | 3/2008 | Hong et al. |
| 2011/0006207 | A1* | 1/2011 | Arjavac .................... G01N 1/32 250/307 |

OTHER PUBLICATIONS

Unknown, "Increasing sample preparation throughput," kleindiek nanotechnik brochure, obtained Mar. 14, 2013, 3 pages.
Unknown, "Micromanipulator for Light Microscopy," http://www.nanotechnik.com/mm3a-Imp.html, obtained Nov. 13, 2013, 1 page.
Stevie, F.A., et al., "Plan view TEM sample preparation using the focused ion beam lift-out technique," AIP Conf. Proc., 1998, vol. 449, No. 868.

* cited by examiner

TEM SAMPLE PREPARATION

This application is a continuation of U.S. patent application Ser. No. 13/930,911, filed Jun. 28, 2013, which is hereby incorporated by reference.

TECHNICAL FIELD OF THE INVENTION

The present invention relates to preparation of samples for viewing in charged particle beam systems.

BACKGROUND OF THE INVENTION

Charged particle beam microscopy, such as scanning ion microscopy and electron microscopy, provides significantly higher resolution and greater depth of focus than optical microscopy. In a scanning electron microscope (SEM), a primary electron beam is focused to a fine spot that scans the surface to be observed. Secondary electrons are emitted from the surface as it is impacted by the primary electron beam. The secondary electrons are detected, and an image is formed, with the brightness at each point on the image being determined by the number of secondary electrons detected when the beam impacts a corresponding spot on the surface. Scanning ion microscopy (SIM) is similar to scanning electron microscopy, but an ion beam is used to scan the surface and eject the secondary electrons.

In a transmission electron microscope (TEM), a broad electron beam impacts the sample and electrons that are transmitted through the sample are focused to form an image of the sample. The sample must be sufficiently thin to allow many of the electrons in the primary beam to travel though the sample and exit on the opposite site. Samples are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface.

Because a sample must be very thin for viewing with transmission electron microscopy (whether TEM or STEM), preparation of the sample can be delicate, time consuming work. The term "TEM" sample as used herein refers to a sample for either a TEM or an STEM and references to preparing a sample for a TEM are to be understood to also include preparing a sample for viewing on an STEM. One method of preparing a TEM sample is to cut the sample from a work piece substrate using an ion beam. A probe is attached to the sample, either before or after the sample has been entirely freed from the work piece. The probe can be attached, for example, by static electricity, FIB deposition, or an adhesive. The sample, attached to the probe, is moved away from the work piece from which it was extracted and typically attached to a TEM grid using FIB deposition, static electricity, or an adhesive.

Figure 1:
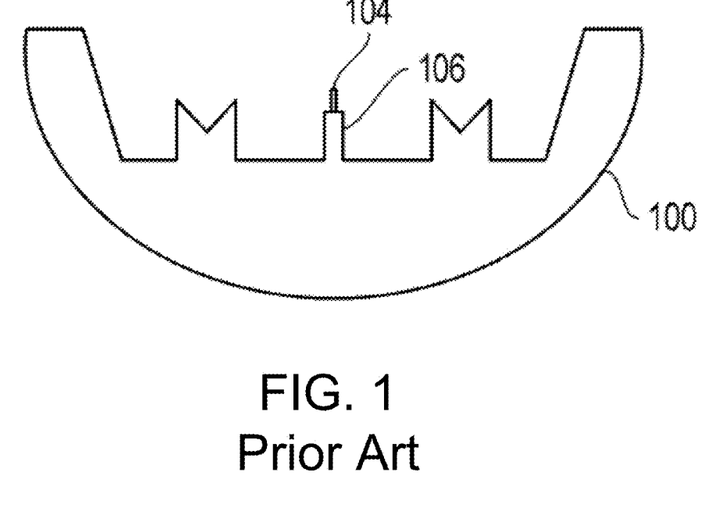
FIG. 1 shows a typical TEM grid to which a sample is attached.

FIG. 1 shows a typical TEM grid 100, which comprises a partly circular 3 mm ring. In some applications, a sample 104 is attached to a finger 106 of the TEM grid by ion beam deposition or an adhesive. The sample extends from the finger 106 so that in a TEM (not shown) an electron beam will have a free path through the sample 104 to a detector under the sample. The TEM grid is typically mounted horizontally onto a sample holder in the TEM with the plane of the TEM grid perpendicular to the electron beam, and the sample is observed.

Some dual beam systems include an ion beam that can be used for extracting the sample, and an electron beam that can be used for SEM or STEM observation. In some dual beam systems, the FIB is oriented an angle, such as 52 degrees, from the vertical and an electron beam column is oriented vertically. In other systems, the electron beam column is tilted and the FIB is oriented vertically or also tilted. The stage on which the sample is mounted can typically be tilted, in some systems up to about 60 degrees.

TEM samples can be broadly classified as "plan view" samples or "cross sectional view" samples, depending on how the sample was oriented on the work piece. If the face of the sample to be observed was parallel to the surface of the work piece, the sample is referred to as a "plan view" sample. If the face to be observed was perpendicular to the work piece surface, the sample is referred to as a "cross sectional view" sample.

Figure 2:
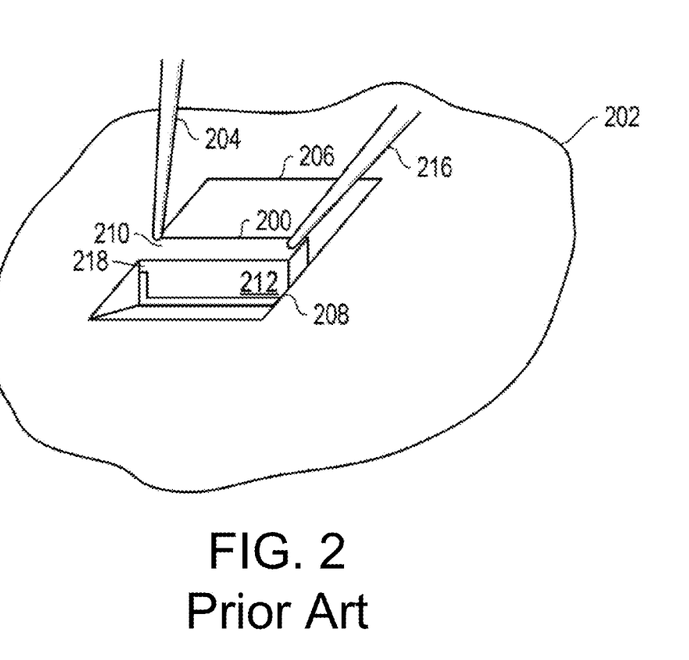
FIG. 2 shows a cross-sectional TEM sample being extracted from a work piece.

FIG. 2 shows a cross-sectional view TEM sample 200 that is partly extracted from a work piece 202 using a typical process. An ion beam 204 cuts trenches 206 and 208 on both side of sample to be extracted, leaving a thin lamella 210 having a major surface 212 that will be observed by an electron beam. The sample 200 is then freed by tilting the work piece 202 in relation to an ion beam, and cutting around its sides and bottom. A probe 216 attaches to the top of the sample 200, before or after it is freed, and transports the sample to a TEM grid. FIG. 2 shows sample 200 almost entirely freed, remaining attached by a tab 218 on one side. FIG. 2 shows ion beam 204 ready to sever tab 218.

Figure 3:
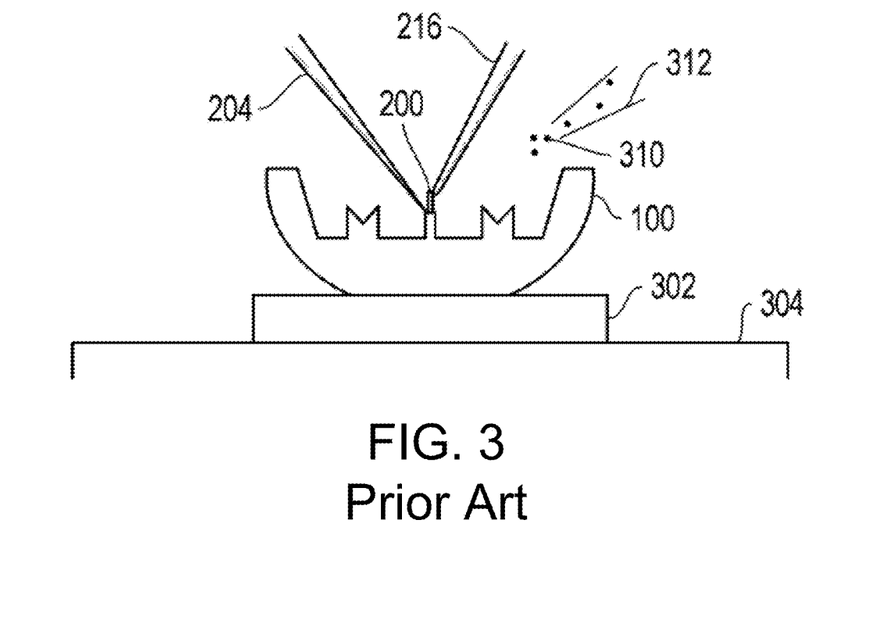
FIG. 3 shows the cross-sectional TEM sample of FIG. 2 being mounted on the TEM grid of FIG. 1.
Figure 4:
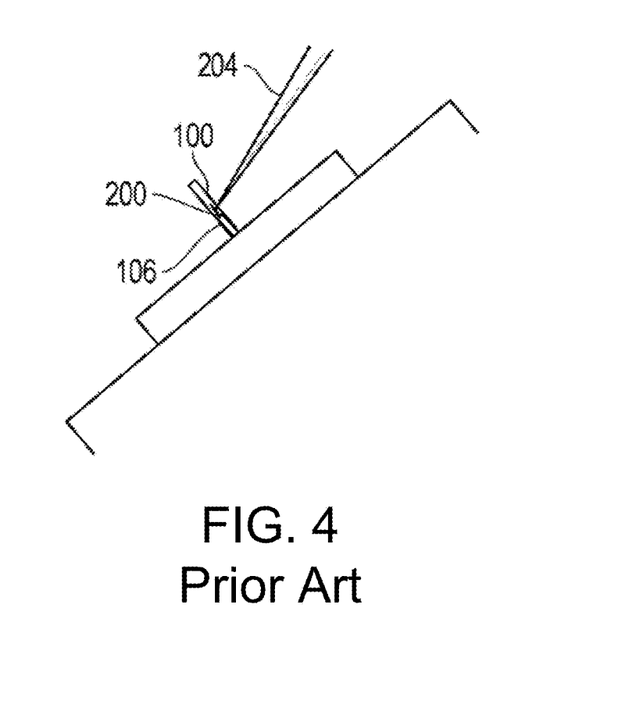
FIG. 4 shows the sample and grid of FIG. 3 tilted and rotated for thinning the sample using an ion beam.

As shown in FIG. 2, the major surface 212 is oriented vertically. Transporting the lamella typically does not change its orientation, so its major surfaces are still oriented vertically when the sample 200 is brought to a TEM sample holder. The plane of the TEM grid 100 is typically oriented vertically as shown in FIG. 3, so that the sample 200 can be attached to the TEM grid in such a way that major surface 212 extends parallel to the plane of the grid, and the grid structure will not interfere with the transmission of electrons when the grid is mounted in a TEM. The ion beam can be used to attach the extracted sample to the TEM grid by ion beam deposition. Once attached, the face of the sample 200 can also be thinned using the ion beam. FIG. 3 shows the sample 200 being attached to the TEM grid 100 in a grid support 302 on a sample stage 304. Sample 200 is attached to grid using an ion beam 204 and a deposition precursor gas 310 from a nozzle 312. FIG. 4 shows that the stage 304 is rotated and tilted so that the sample 200 is substantially perpendicular to the ion beam 204 so that the sample 200 can be thinned by the ion beam.

Figure 5:
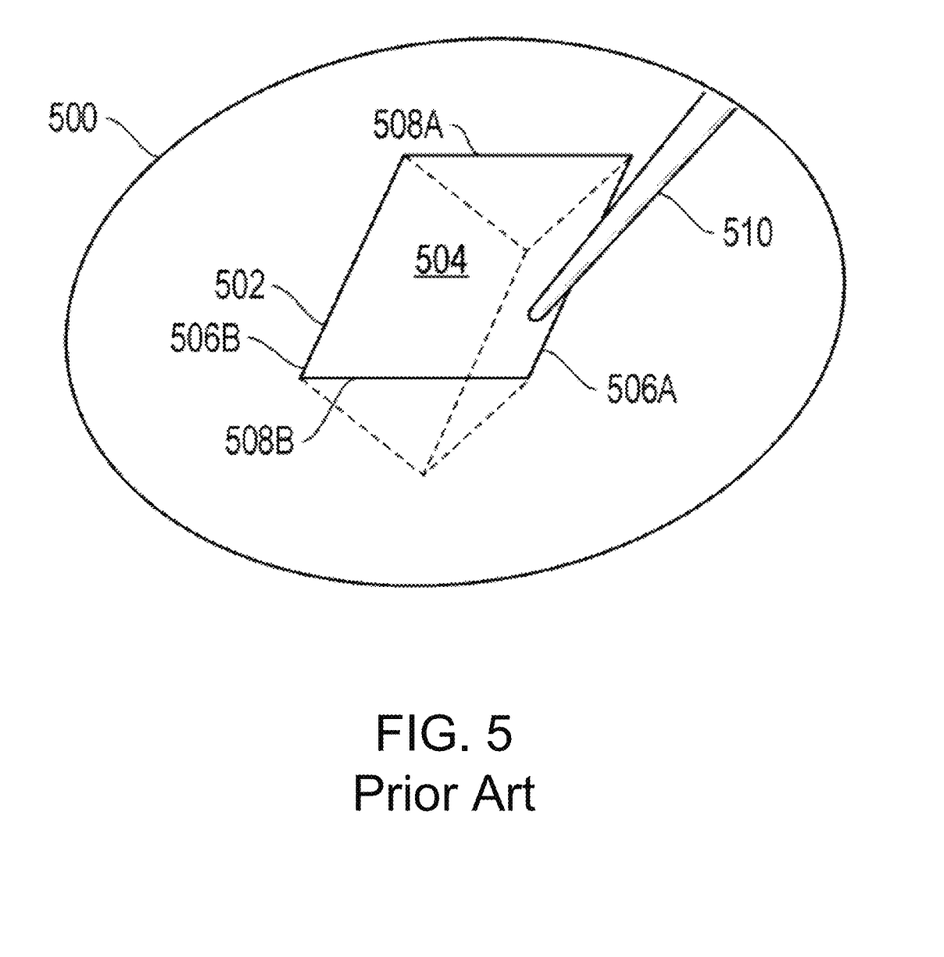
FIG. 5 shows a TEM sample being extracted from a work piece.

FIG. 5 shows a work piece 500 from which a plan view sample 502 is being extracted to view a face 504 of the sample. The sample 502 is undercut by two intersecting ion beam cuts 506A and 506B from opposite directions, and then the ion beam cuts the sides 508A and 508B to substantially free a portion of the work piece 500 that includes sample 502. A probe 510 is attached to the top of the sample 502. The extracted sample is therefore oriented horizontally. If the sample were attached in a horizontal orientation to a vertically oriented TEM grid, the sample would extend normal to the plane of the grid, and the grid would interfere with the electron beam of the TEM. If the sample were mounted in a horizontally oriented TEM grid, the face 504 to be observed would face upward. It would then be difficult in a conventional FIB system to thin the back side of the plan view sample 502 without removing the TEM grid from the vacuum chamber and flipping it over to expose the back side of sample 502 for thinning.

This problem of the orientation of a plan view TEM sample 502 has been overcome in the past by using a "flip stage," on which the TEM grid can be oriented horizontally for attaching the plan view sample, and then the stage can be flipped 180 degrees and rotated so that the backside of the sample can be presented normal to the ion beam for thinning. A flip stage is described for example in U.S. Pat. No. 6,963,068 to Asselbergs et al. for "Method for the manufacture and transmissive irradiation of a sample, and particle-optical system" and provides a degree of freedom not available on conventional stages. Such flip stages are expensive and not available in all FIB systems.

In addition, it is desirable to make plan view samples suitable for ex-situ liftout. Ex-situ liftout comprises leaving the thin lamella in a wafer and then extracting the lamella in a separate bench-top system using an extraction device such as a glass needle. Presently, there is not a way to extract a plan view sample for ex-situ liftout from a full wafer or similar substrate. What is needed is a way to reorient a plan view sample so that the orientation of the plan view sample is changed from being substantially horizontal relative to the surface of the wafer to substantially vertical relative to the surface of the wafer.

SUMMARY OF THE INVENTION

An object of the invention is to provide a method and apparatus for altering the orientation of a charged particle beam sample. Embodiments of the method includes providing a first work piece on a sample stage having a sample stage plane, the first work piece including a lamella plane in a first orientation. A sample is milled from the first work piece using an ion beam so that the sample is substantially free from the first work piece. A probe is attached to the sample, the probe including a shaft having a shaft axis, the shaft axis oriented at a shaft angle in relation to the sample stage plane, the shaft angle being non-normal to the sample stage plane. The probe is rotated about the shaft axis through a rotational angle so that the lamella plane is in a second orientation. The sample is attached to or placed on the sample on either the first work piece, the first work piece being the work piece from which the sample was milled, or on a second work piece, the second work piece being a work piece from which the sample was not milled. The sample is thinned using the ion beam to form a lamella, the lamella being oriented in the lamella plane.

Embodiments of the apparatus include an ion beam column, a sample stage, a probe, and a controller. The sample stage includes a sample stage plane and is capable of moving in at least two dimensions and of rotating about a vertical axis. The probe is rotatable around a shaft axis. The shaft axis is oriented at a shaft angle in relation to the sample stage plane. The shaft angle is non-normal to the sample stage plane. The controller causes the ion beam column, the sample stage, the probe, to perform the steps of supporting a first work piece on the sample stage, the first work piece including a lamella plane; milling a sample from the first work piece using an ion beam from the ion beam column so that the sample is substantially free from the first work piece; attaching the probe to the sample; rotating the probe about the shaft axis through a rotational angle; attaching the sample to or placing the sample on the first work piece, the first work piece being the work piece from which the sample was milled or a second work piece, the second work piece being a work piece from which the sample was not milled; and thinning the sample using the ion beam column to form a lamella, the lamella being oriented in the lamella plane.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more through understanding of the present invention, and advantages thereof, reference is now made to the following descriptions taken in conjunction with the accompanying drawings, in which.

DETAILED DESCRIPTION OF PREFERRED EMBODIMENTS

This disclosure relates to novel methods for preparing a plan view sample for ex-situ liftout. In one embodiment, the invention facilitates preparation of a plan view sample for viewing in TEMs or STEMs. The methods provide for extracting and mounting a plan view sample onto a TEM grid in such a manner that the sample can be extracted, attached, and thinned without requiring a flip stage and without requiring that the TEM grid to be removed from the vacuum chamber and reoriented. Re-orienting the sample may also facilitate other analytical or processing operations on the sample.

Figure 6:
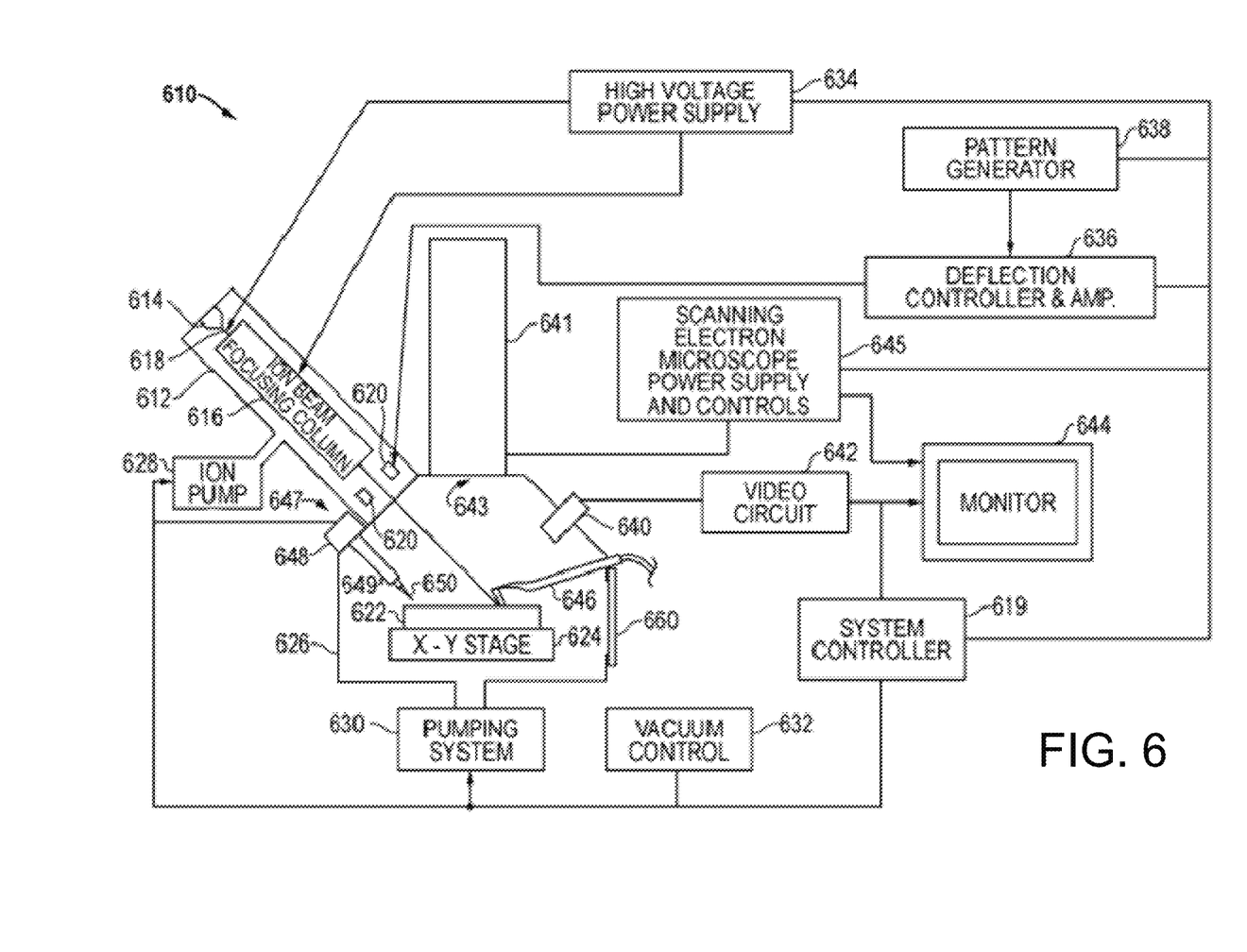
FIG. 6 shows a typical dual beam system used to implement the present invention.

FIG. 6 shows a typical ion beam system, focused ion beam (FIB) system 610, suitable for practicing the present invention. FIB system 610 includes an evacuated envelope having an upper neck portion 612 within which are located a liquid metal ion source 614 or other ion source and a focusing column 616. Other types of ion sources, such as multicusp or other plasma sources, and other optical columns, such as shaped beam columns, could also be used, as well as electron beam and laser system.

An ion beam 618 passes from liquid metal ion source 614 through ion beam focusing column 616 and between electrostatic deflection means schematically indicated at deflection plates 620 toward work piece 622, which comprises, for example, a semiconductor device positioned on stage 624 within lower chamber 626. Stage 624 can also support one or more TEM sample holders, so that a sample can be extracted from the semiconductor device and moved to a TEM sample holder. Stage 624 can preferably move in a horizontal plane (X and Y axes) and vertically (Z axis). Stage 624 can also tilt approximately sixty (60) degrees and rotate about the Z axis. A system controller 619 controls the operations of the various parts of FIB system 610. Through system controller 619, a user can control ion beam 618 to be scanned in a desired manner through commands entered into a conventional user interface (not shown). Alternatively, system controller 619 may control FIB system 610 in accordance with programmed instructions.

For example, a user can delineate a region of interest on a display screen using a pointing device, and then the system could automatically perform the steps described below to extract a sample. In some embodiments, FIB system 610 incorporates image recognition software, such as software commercially available from Cognex Corporation, Natick, Mass., to automatically identify regions of interest, and then the system can manually or automatically extract samples in accordance with the invention. For example, the system could automatically locate similar features on semiconductor wafers including multiple devices, and take samples of those features on different (or the same) devices.

An ion pump 628 is employed for evacuating upper neck portion 612. The lower chamber 626 is evacuated with turbomolecular and mechanical pumping system 630 under the control of vacuum controller 632. The vacuum system provides within lower chamber 626 a vacuum of between approximately $1 \times 10^{-7}$ Torr ($1.3 \times 10^{-7}$ mbar) and $5 \times 10^{-4}$ Torr ($6.7 \times 10^{-4}$ mbar). If an etch-assisting gas, an etch-retarding gas, or a deposition precursor gas is used, the chamber background pressure may rise, typically to about $1 \times 10^{-5}$ Torr ($1.3 \times 10^{-5}$ mbar).

High voltage power supply 634 is connected to liquid metal ion source 614 as well as to appropriate electrodes in ion beam focusing column 616 for forming an approximately 1 keV to 60 keV ion beam 618 and directing the same toward a sample. Deflection controller and amplifier 636, operated in accordance with a prescribed pattern provided by pattern generator 638, is coupled to deflection plates 620 whereby ion beam 618 may be controlled manually or automatically to trace out a corresponding pattern on the upper surface of work piece 622. In some systems the deflection plates are placed before the final lens, as is well known in the art. Beam blanking electrodes (not shown) within ion beam focusing column 616 cause ion beam 618 to impact onto blanking aperture (not shown) instead of target 622 when a blanking controller (not shown) applies a blanking voltage to the blanking electrode.

The liquid metal ion source 614 typically provides a metal ion beam of gallium. The source typically is capable of being focused into a sub one-tenth micrometer wide beam at work piece 622 for either modifying the work piece 622 by ion milling, enhanced etch, material deposition, or for the purpose of imaging the work piece 622. A charged particle detector 640, such as an Everhart Thornley or multi-channel plate, used for detecting secondary ion or electron emission is connected to a video circuit 642 that supplies drive signals to video monitor 644 and receiving deflection signals from controller 619.

The location of charged particle detector 640 within lower chamber 626 can vary in different embodiments. For example, a charged particle detector 640 can be coaxial with the ion beam and include a hole for allowing the ion beam to pass. In other embodiments, secondary particles can be collected through a final lens and then diverted off axis for collection. A scanning electron microscope (SEM) 641, along with its power supply and controls 645, are optionally provided with the FIB system 610.

A gas delivery system 646 extends into lower chamber 626 for introducing and directing a gaseous vapor toward work piece 622. U.S. Pat. No. 5,851,413 to Casella et al. for "Gas Delivery Systems for Particle Beam Processing," assigned to the assignee of the present invention, describes a suitable gas delivery system 646. Another gas delivery system is described in U.S. Pat. No. 5,435,850 to Rasmussen for a "Gas Injection System," also assigned to the assignee of the present invention. For example, iodine can be delivered to enhance etching, or a metal organic compound can be delivered to deposit a metal.

A micromanipulator 647, such as the EasyLift™ NanoManipulator System from FEI Company, Hillsboro, Oreg., assignee of the present invention, the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 647 may comprise precision electric motors 648 positioned outside the vacuum chamber to provide X, Y, Z, and theta control of a portion 649 positioned within the vacuum chamber. The micromanipulator 647 can be fitted with different end effectors for manipulating small objects. In the embodiments described below, the end effector is a thin probe 650. The thin probe 650 may be electrically connected to system controller 619 to apply an electric charge to the probe 650 to control the attraction between a sample and the probe.

A door 660 is opened for inserting work piece 622 onto X-Y stage 624, which may be heated or cooled, and also for servicing an internal gas supply reservoir, if one is used. The door is interlocked so that it cannot be opened if the system is under vacuum. The high voltage power supply provides an appropriate acceleration voltage to electrodes in ion beam focusing column focusing 616 for energizing and focusing ion beam 618. When it strikes work piece 622, material is sputtered, that is physically ejected, from the sample. Alternatively, ion beam 618 can decompose a precursor gas to deposit a material. Focused ion beam systems are commercially available, for example, from FEI Company, Hillsboro, Oreg., the assignee of the present application. While an example of suitable hardware is provided above, the invention is not limited to being implemented in any particular type of hardware.

Figure 7:
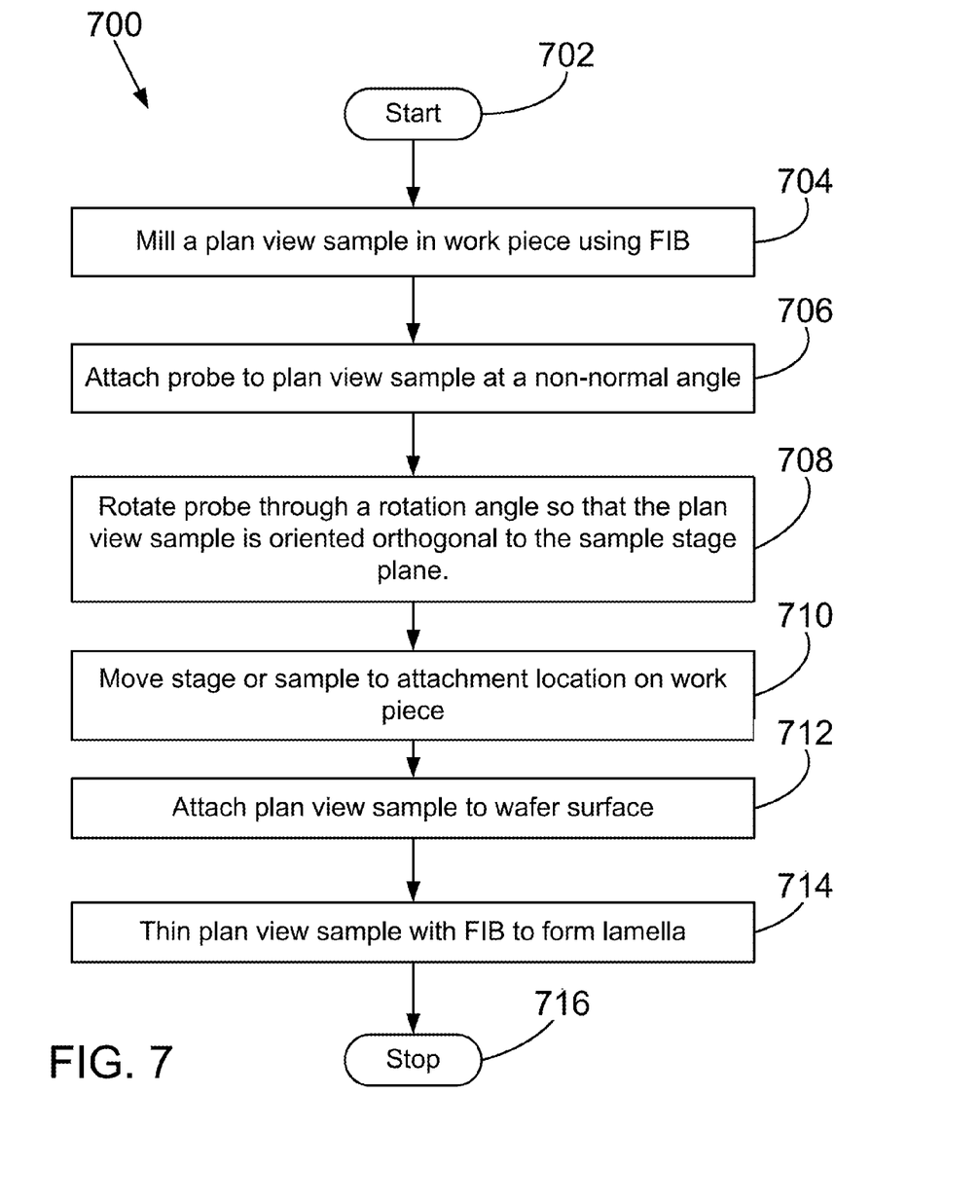
FIG. 7 is a flow chart showing the steps of a preferred embodiment of the present invention.
Figure 8:
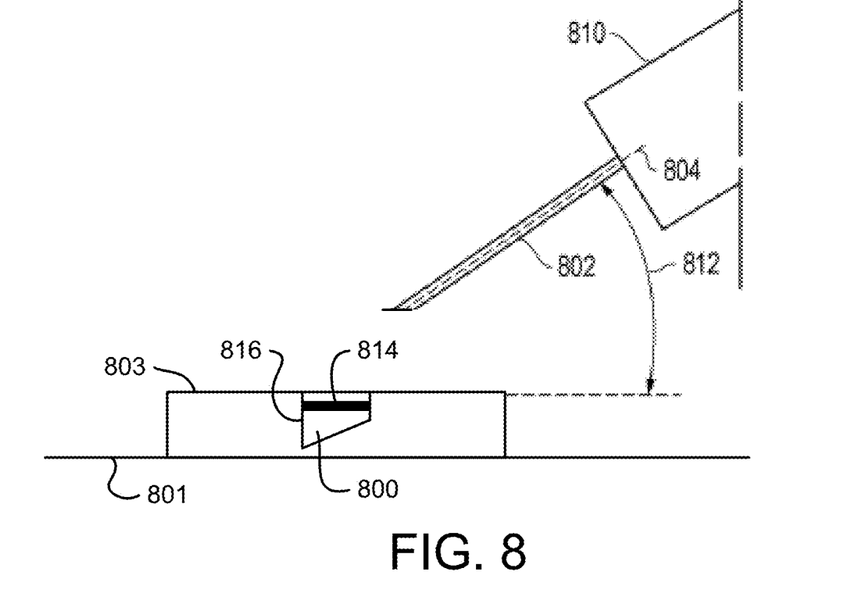
FIG. 8 shows plan view sample 800 formed in work piece 803.

FIG. 7 describes the steps of a preferred method of preparing a plan view TEM sample. The process begins at start block 702. In step 704, an ion beam, preferably a focused ion beam, mills a plan view sample in the work piece, substantially or completely freeing the sample from the work piece. FIG. 8 shows plan view sample 800 formed in work piece 803. Plan view sample 800 includes a lamella plane 814 that is substantially parallel to the plane of sample stage 801 and/or the top surface of the work piece 803. The lamella that is formed in accordance with this method is oriented in the lamella plane

814. In a preferred embodiment of the present invention, sample 800 is milled so that at least one face 816 of the milled sample is substantially perpendicular to lamella plane 814.

Figure 9:
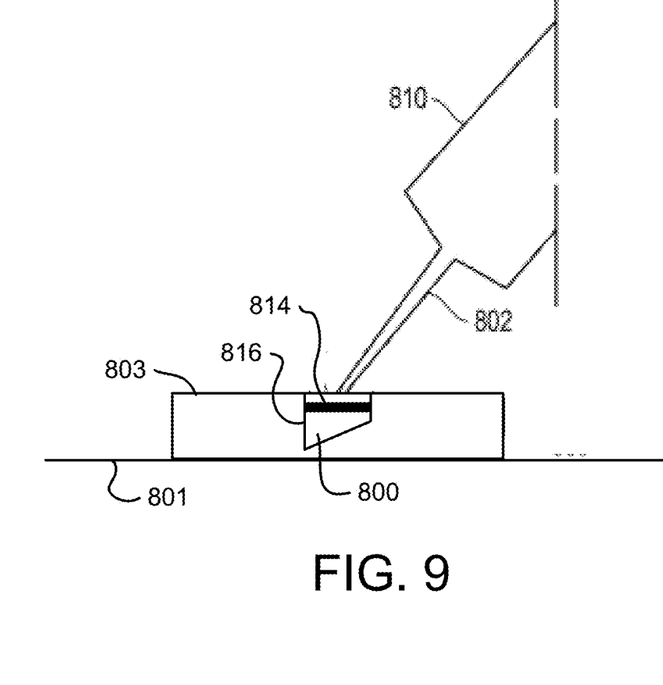
FIG. 9 shows probe 802 attached to sample 800.

In step 706, a probe 802 having a shaft axis 804 is attached to sample 800. Probe 802 can be attached to sample 800 by ion beam deposition. Alternatively, probe 802 can be attached to sample 800 by an adhesive or other means known to a skilled artisan. Probe shaft 802 is attached to a micromanipulator 810, which can move probe 802 in three dimensions and can rotate probe 802 about shaft axis 804. Probe 802 preferably remains at a fixed angle 812 to the plane of the sample stage when the sample stage is in its untilted orientation. Angle 812 is non-normal to sample stage plane 801 (or the top surface of work piece 803). Angle 812 is preferably 45 degrees to the sample stage plane (or top surface of work piece 803). The tip of probe 802 is preferably cut at the same angle as angle 812, so that the flat area of the probe tip is parallel to the plane of the sample stage in its untilted orientation. The probe is attached to the sample 800 as shown in FIG. 9. The probe 800 can be attached, for example, using focused ion beam deposition of a metal, such as tungsten, to the sample and the probe. To attach probe 802 to sample 800, the probe tip is preferably brought near the top surface of sample 800 and attached to sample 800 by ion beam deposition, as described, for example, in U.S. Pat. No. 7,615,745 to Schampers et al., which is incorporated by reference in its entirety into the present specification. A precursor gas, such as tungsten hexacarbonyl, $W(CO)_6$, is directed toward the gap between the tip of probe 802 and sample 800, as the ion beam is directed to scan the area around the point of contact. The ion beam is used to induce decomposition of the precursor gas to deposit a material that bridges the gap and connects the sample 800 to the tip of probe 802. In alternative embodiments, probe 800 is brought into contact with the top surface of sample 800 and attached to sample 800 by ion beam deposition, by use of an adhesive, by means of attractive forces (e.g., electrostatic, Van der Waals, etc.) between sample 800 and probe 802, or by other suitable means known in the art.

Figure 10:
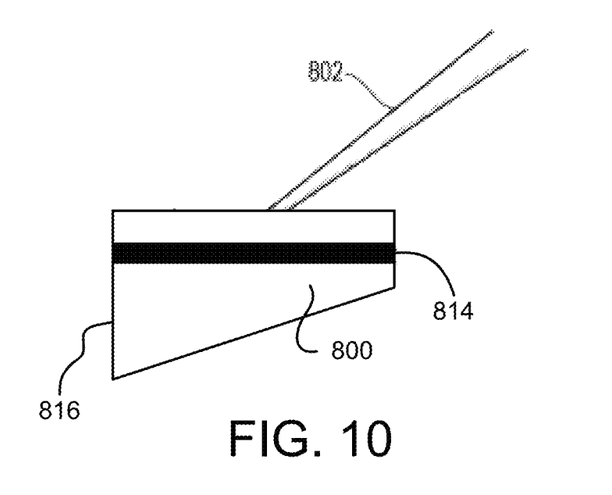
FIG. 10 shows sample 800 removed from work piece 803 before probe 802 is rotated through the non-zero rotational angle.
Figure 11:
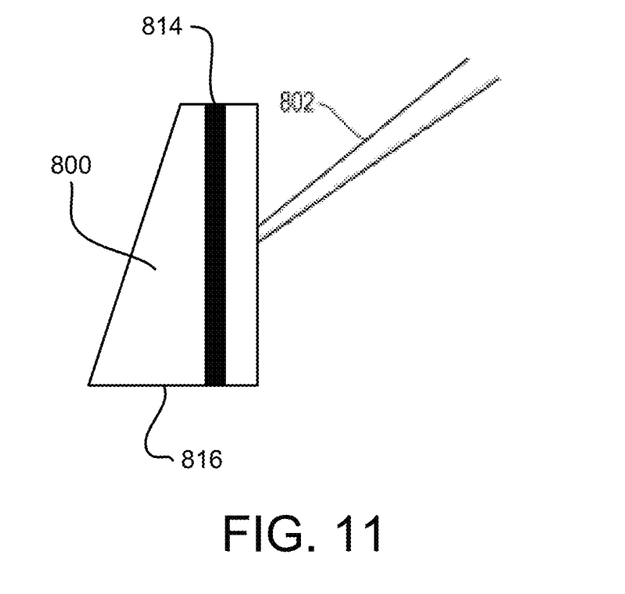
FIG. 11 shows sample 800 removed from work piece 803 after probe 802 is rotated through the non-zero rotational angle.

In step 708, probe 802 is rotated about shaft axis 804 through a non-zero rotational angle. Sample 800 may need to be lifted out from work piece 803 for a distance so that sample 800 has clearance to rotate as probe 802 is rotated. FIG. 10 shows sample 800 removed from work piece 803 before probe 802 is rotated. FIG. 11 shows sample 800 removed from work piece 803 after probe 802 is rotated through the non-zero rotational angle. The rotation of probe 802 causes sample 800 to be re-oriented so that lamella plane 814 is substantially perpendicular to the top surface of work piece 803 and sample stage plane 801. Once sample 800 is re-oriented so that lamella plane 814 is substantially perpendicular to the top surface of work piece 803 and sample stage plane 801, sample 800 can be processed like a cross-section view sample. In a preferred embodiment, angle 812 between the probe and the sample stage plane is 45 degrees and the rotational angle is 180 degrees. That is, by rotating the probe 180 degrees about shaft axis 812, lamella plane 814 is re-oriented from being substantially parallel to the sample stage plane to being substantially perpendicular to the sample stage plane.

Figure 12:
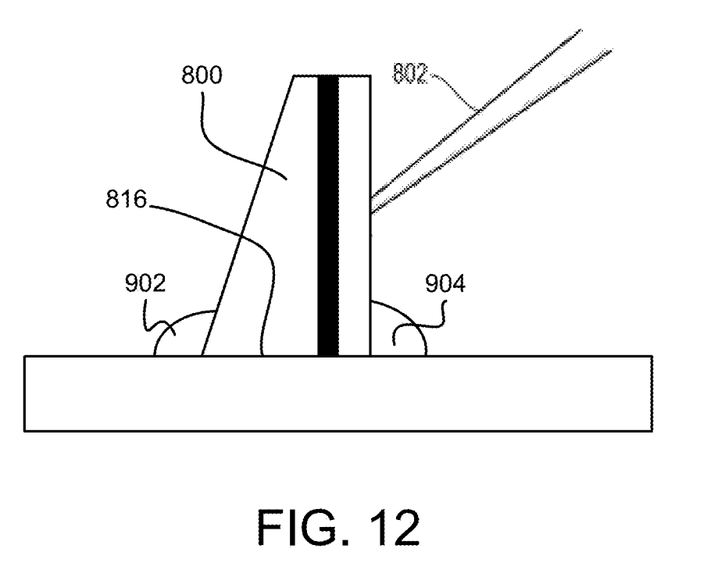
FIG. 12 shows a sample 800 disposed at the attachment location on work piece 803 after probe 802 is rotated through the non-zero rotational angle.

In step 710, sample 800 is preferably moved to an attachment location on the same work piece surface, as shown in FIG. 12. In alternative embodiments, sample 800 is moved to an attachment location on a different work piece. References to the attachment location on work piece surface 803 are to be understood to refer to an attachment location on either the same work piece or on a different work piece. Either probe 802 can be moved or the sample stage can be moved to relocate sample 800 to the attachment location. The attachment location is a location on work piece surface 803 where face 816 of sample 800 is brought into close proximity or in direct contact with work piece surface 803 and attached for further processing. In step 712, sample 800 is then attached to work piece surface 803, preferably using ion beam deposition. The ion beam is directed through a precursor gas to form one or more depositions 902-904. Depositions 902-904 are attached to both sample 800 and work piece surface 803 thereby fastening sample 800 to work piece surface 803. In alternative embodiments, sample 800 is placed on work piece surface 803 and held in place by use of an adhesive, by means of attractive forces (e.g., electrostatic, Van der Waals, etc.) between sample 800 and work piece surface 803, or by other suitable means known in the art. In some embodiments, a recessed area that substantially fits sample 800 is milled in work piece surface 803 at the attachment location to make the drop off of the sample 800 more reliable. Once sample 800 is attached to work piece surface 803 at the attachment location, probe 802 can be detached from sample 800, preferably using the FIB to sever the connection.

Figure 13:
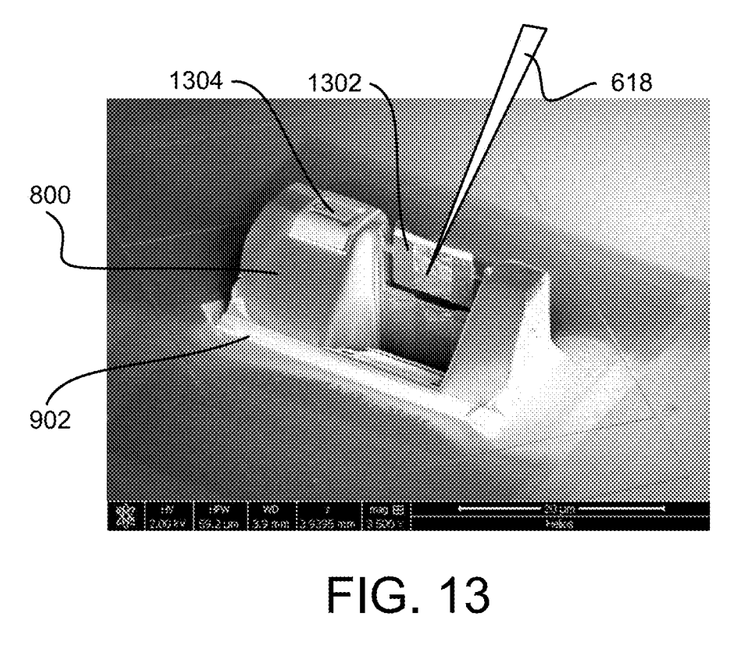
FIG. 13 shows sample 800 thinned by ion beam 618 at the attachment location on work piece 803 to form a lamella 1302.

In step 714, sample 800 is thinned by ion beam 618 at the attachment location on work piece 803 to form a lamella 1302, as shown in FIG. 13. Fiducial 1304 can be used for quickly locating lamella plane 814 and for determining the appropriate amount of ion beam milling to perform to form lamella 1302. Lamella 1302 will be oriented substantially perpendicular to the top surface of work piece 803 and sample stage plane 801. Lamella 1302 is therefore in the same orientation as a lamella formed from a cross-section sample. Once sufficiently thinned and processed, lamella 1302 can be freed from sample 800 and placed on a TEM grid for viewing in an S/TEM instrument.

Skilled persons will also recognize that the flat surface on the bottom of the probe, while preferred, can be eliminated in some embodiments. As long as the sample is fixed to the probe, rotating the probe will re-orient the sample, with the re-orientation angle being determined by the degree of rotation and the angle between the probe axis and the stage plane. Thus, a rounded probe tip, a probe tip angle in which the probe tip is not parallel to the stage plane, or any other probe tip shape, is within the scope of the invention.

Although the present invention and its advantages have been described in detail, it should be understood that various changes, substitutions and alterations can be made herein without departing from the spirit and scope of the invention as defined by the appended claims. For example, the angles and orientations described are useful for a system with an ion beam oriented at an angle to the vertical. For an ion beam column that is oriented vertically, or at any other angle, a skilled person can readily alter the example described above to provide an appropriate embodiment of the invention. The invention is useful not only for TEM sample preparation, but can be used for SEM or optical microscope observation, or for any charged particle beam, laser, or other operation on a microscopic specimen.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include

I claim as follows:

1. A method for creating a TEM sample, comprising:
   providing a first work piece on a sample stage having a sample stage plane, the first work piece including a lamella plane being oriented in a first orientation;
   milling a sample from the first work piece using an ion beam so that the sample is substantially free from the first work piece;
   attaching a probe to the sample, the probe including a shaft having a shaft axis, the shaft axis oriented at a shaft angle in relation to the sample stage plane, the shaft angle being non-normal to the sample stage plane;
   rotating the probe about the shaft axis through a rotational angle, the rotation causing the sample to be rotated so that the lamella plane is oriented in a second orientation;
   attaching the sample to or placing the sample on:
      the first work piece, the first work piece being the work piece from which the sample was milled; or
      a second work piece, the second work piece being a work piece from which the sample was not milled.

2. The method of claim 1 in which the shaft angle is 45 degrees and the rotational angle is 180 degrees.

3. The method of claim 1 in which attaching the probe to the sample includes attaching the probe to the sample by ion beam deposition.

4. The method of claim 1 in which attaching the probe to the sample includes attaching the probe to the sample by an adhesive.

5. The method of claim 1 in which milling the sample from the first work piece using an ion beam includes milling the sample from the first work piece using a focused ion beam.

6. The method of claim 1 in which milling the sample further comprises milling the sample so that one face of the milled sample is substantially perpendicular to the lamella plane.

7. The method of claim 1 in which attaching the sample to the first or second work piece further comprises forming at least one deposition on the work piece and the sample, the deposition attaching the sample to the first or second work pieces.

8. The method of claim 7 further comprising forming the at least one deposition by ion beam deposition using the ion beam.

9. The method of claim 1 in which attaching the sample to or placing the sample on the first or second work piece further comprises milling a recessed area in a surface of the first or second work piece, the recessed area being of a size that suitable to receive at least a portion of the sample, and placing the sample so that at least a portion of the sample is disposed within the recessed area.

10. The method of claim 1 in which rotating the probe about the shaft axis through a rotational angle causes the sample to be rotated so that the sample stage plane and the lamella plane are substantially perpendicular.

11. The method of claim 10 in which prior to the milling step the lamella plane is substantially parallel to the sample stage plane.

12. The method of claim 1 further comprising:
   milling the lamella from the sample using an ion beam so that the lamella is substantially free from the sample;
   attaching the lamella to a transmission electron microscope (TEM) grid; and
   viewing the lamella while attached to the transmission electron microscope (TEM) grid.

13. The method of claim 12 further comprising, prior to milling the lamella from the sample, moving the work piece upon which the sample is attached or placed to a second device, the second device being a device that was not used to mill the sample from the work piece.

* * * * *